United States Patent
Sheu et al.

(10) Patent No.: US 8,968,182 B2
(45) Date of Patent: Mar. 3, 2015

(54) IMPLANTABLE MESH COMBINING BIODEGRADABLE AND NON-BIODEGRADABLE FIBERS

(71) Applicant: Boston Scientific Scimed, Inc., Maple Grove, MN (US)

(72) Inventors: Min-Shyan Sheu, Chelmsford, MA (US); Jamie Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/275,039

(22) Filed: May 12, 2014

(65) Prior Publication Data

US 2014/0249362 A1    Sep. 4, 2014

Related U.S. Application Data

(63) Continuation of application No. 11/448,252, filed on Jun. 6, 2006, now Pat. No. 8,721,519.

(51) Int. Cl.
*A61F 2/02* (2006.01)
*A61F 2/00* (2006.01)
*A61L 31/14* (2006.01)
*A61M 37/00* (2006.01)

(52) U.S. Cl.
CPC ............ *A61F 2/0063* (2013.01); *A61F 2/0045* (2013.01); *A61L 31/148* (2013.01); *A61M 37/0069* (2013.01); *A61F 2250/0031* (2013.01); *A61L 2430/22* (2013.01); *A61F 2002/0068* (2013.01)
USPC .................. 600/37; 606/151; 600/30

(58) Field of Classification Search
CPC .... A61F 2/0036; A61F 2/0045; A61F 2/0063
USPC .................. 600/29–32, 37; 606/151; 623/23.72–23.76
See application file for complete search history.

(56) References Cited

U.S. PATENT DOCUMENTS

| | | |
|---|---|---|
| 3,463,158 A | 8/1969 | Schmitt et al. |
| 4,585,458 A | 4/1986 | Kurland |
| 4,693,720 A | 9/1987 | Scharnberg et al. |
| 5,795,584 A | 8/1998 | Totakura et al. |
| 6,042,534 A | 3/2000 | Gellman et al. |
| 6,852,330 B2 | 2/2005 | Bowman et al. |
| 8,721,519 B2 | 5/2014 | Sheu et al. |
| 2005/0010078 A1 | 1/2005 | Jamiolkowski et al. |

(Continued)

FOREIGN PATENT DOCUMENTS

| | | |
|---|---|---|
| EP | 1520552 A1 | 4/2005 |
| JP | 2005-534422 A | 11/2005 |

(Continued)

OTHER PUBLICATIONS

Final Office Action for U.S. Appl. No. 11/448,252, mailed on Aug. 12, 2013, 13 pages.

(Continued)

*Primary Examiner* — Charles A Marmor, II
*Assistant Examiner* — Carrie R Dorna

(57) ABSTRACT

Disclosed are mesh materials adapted for use in an implantable sling. The mesh materials include biodegradable and non-degradable components that may be adapted to facilitate scar-tissue ingrowth as the biodegradable components degrade.

20 Claims, 4 Drawing Sheets

(56) References Cited

U.S. PATENT DOCUMENTS

| | | |
|---|---|---|
| 2005/0070930 A1 | 3/2005 | Kammerer |
| 2005/0096499 A1 | 5/2005 | Li et al. |
| 2005/0288797 A1 | 12/2005 | Howland |

FOREIGN PATENT DOCUMENTS

| | | |
|---|---|---|
| WO | 2002/078568 A1 | 10/2002 |
| WO | 2004/012579 A2 | 2/2004 |
| WO | 2006/002340 A2 | 1/2006 |
| WO | 2007/145974 A2 | 12/2007 |

OTHER PUBLICATIONS

Final Office Action for U.S. Appl. No. 11/448,252, mailed on Jul. 3, 2012, 16 pages.
Final Office Action for U.S. Appl. No. 11/448,252, mailed on Nov. 5, 2010, 13 pages.
Non-Final Office Action for U.S. Appl. No. 11/448,252, mailed on Apr. 8, 2010, 12 pages.
Non-Final Office Action for U.S. Appl. No. 11/448,252, mailed on Dec. 19, 2012, 16 pages.
Non-Final Office Action for U.S. Appl. No. 11/448,252, mailed on Jan. 26, 2012, 16 pages.
Non-Final Office Action for U.S. Appl. No. 11/448,252, mailed on Oct. 4, 2011, 16 pages.
Notice of Allowance received for U.S. Appl. No. 11/448,252, mailed Dec. 18, 2013, 10 pages.
Office Action Received for Japanese Patent Application No. 2009-514345 (with Translation), mailed on Feb. 6, 2014, 12 pages.
Response to Non Final Office Action for U.S. Appl. No. 11/448,252, filed Apr. 25, 2012, 13 pages.
Response to Non Final Office Action for U.S. Appl. No. 11/448,252, filed Feb. 7, 2011, 9 pages.
Response to Non Final Office Action for U.S. Appl. No. 11/448,252, filed May 1, 2013, 8 pages.
Response to Non Final Office Action for U.S. Appl. No. 11/448,252, filed Nov. 12, 2013, 8 pages.
Response to Non Final Office Action for U.S. Appl. No. 11/448,252, filed Nov. 16, 2011, 11 pages.
Response to Non Final Office Action for U.S. Appl. No. 11/448,252, filed Oct. 6, 2010, 12 pages.
"Hainyou Shogai Practice", vol. 12, No. 2, 2004, pp. 168-175.
"Grid", the American Heritage Dictionary of the English Language, Boston: Houghton Mifflin, 2007, Credo Reference, Web. 26, Oct. 2010.
"Mesh" Collins English Dictionary, London: Collins, 2000, Credo Reference, Web. Oct. 26, 2010.
Final Office Action for Japanese Patent Application No. 2009-514345 (with Translation), mailed on May 30, 2014, 10 pages.

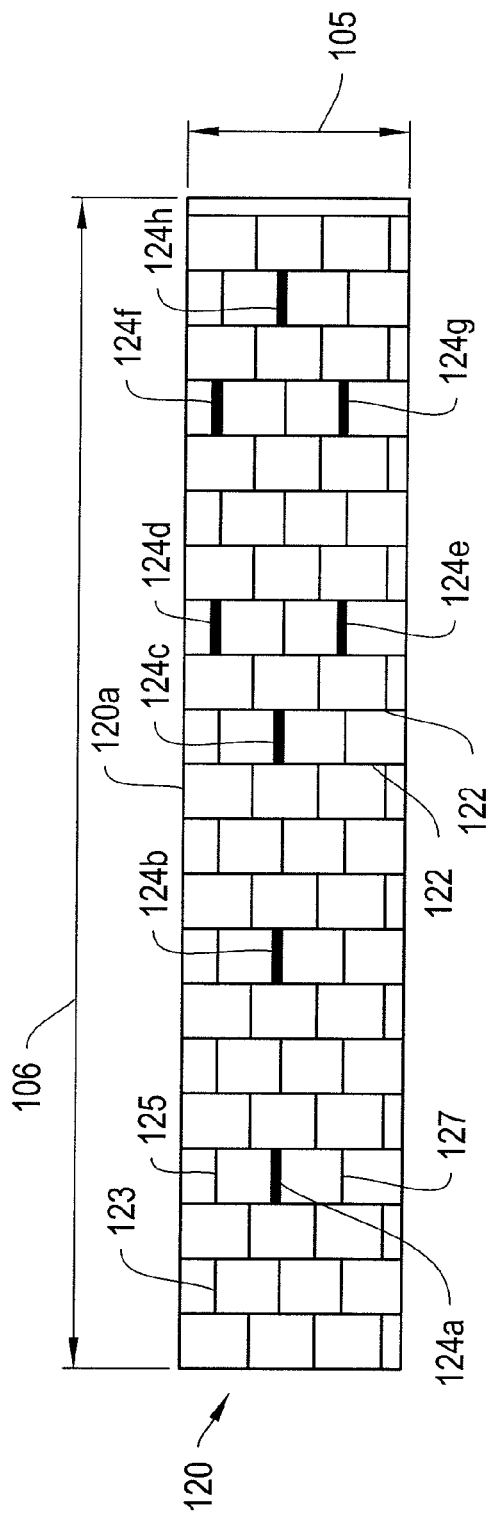
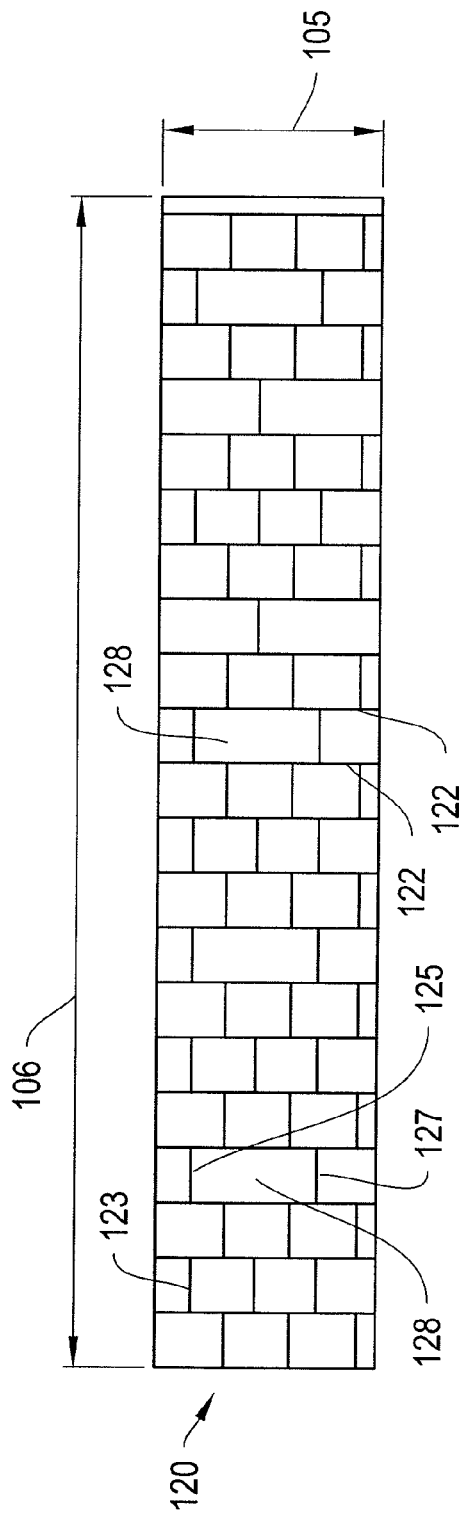

IMPLANTABLE MESH COMBINING BIODEGRADABLE AND NON-BIODEGRADABLE FIBERS

CROSS-REFERENCE TO RELATED APPLICATIONS

This application is a Continuation of, and claims priority to, U.S. patent application Ser. No. 11/448,252, filed on Jun. 6, 2006, entitled "IMPLANTABLE MESH COMBINING BIODEGRADABLE AND NON-BIODEGRADABLE FIBERS", the disclosure of which is incorporated by reference herein in its entirety.

FIELD OF THE INVENTION

The invention generally relates to surgically implantable supportive slings. More specifically, in various embodiments, the invention is directed to mesh slings including biodegradable fibers interwoven with non-biodegradable fibers. In some embodiments, fibers include both biodegradable and non-biodegradable portions. The invention also relates to methods of use and manufacture of such slings and fibers.

BACKGROUND

Urinary incontinence affects over 13 million men and women in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results. Moreover, the condition of stress urinary incontinence is often compounded by the presence of untreated vaginal vault prolapse or other more serious pelvic floor disorders. Often, treatments of stress incontinence are made without treating the pelvic floor disorders, potentially leading to an early recurrence of the pelvic floor disorder.

These and related conditions, are often treated using an implantable supportive sling. Such slings may be made from a variety of materials, but are often made from a mesh material. The mesh may be placed, for example, under the urethra, close to the high-pressure zone with little or no elevation to the urethra. When abdominal pressure increases, such as from coughing, sneezing, or the like, the sling facilitates the collapse of the urethra as a mechanism for closing the urethra to inhibit urine leakage.

Subsequent to implantation, scar tissue typically forms around the sling. This scar tissue further supports the urethra and sphincter muscle to facilitate complete urethral closure. Clinically, there are two major challenges to a successful outcome—the formation of prominent and permanent scar tissue around the sling, and release of the sling tension to accommodate the body growth. There is a need for an improved surgically implantable sling that better addresses these two challenges.

SUMMARY OF THE INVENTION

The invention addresses the deficiencies of the prior art by providing an improved implantable sling for supporting an anatomical site in the body of a patient. More particularly, in various aspects, the invention provides a supportive sling formed from a material that encourages prominent and permanent formation of scar tissue upon sling implantation and optimizes the sling tension post-surgery using a combination of non-biodegradable materials with biodegradable materials. According to one feature, as portions of the sling degrade, they are replaced by scar tissue, which provides for automatic sling tension attenuation in response, for example, to body movement and body growth. According to another feature, the biodegradable materials are integrated into the sling in such a way that pores/interstitial gaps in the sling enlarge as the materials degrade, further assisting in tissue in-growth and scar tissue formation. According to a further feature, the degradation products of the biodegradable materials accelerate tissue inflammation and thus, scar tissue formation onto and/or into the implanted sling.

More particularly, in one aspect, the invention provides a mesh sling including a plurality of fibers that are braided, knitted or otherwise woven together. The sling fibers may be formed from one or more filaments, which may be made from one or more materials, or may be formed as monofilaments. According to one embodiment, some of the sling fibers are biodegradable, while others are non-biodegradable. In one configuration, the sling has a high biodegradable/non-biodegradable ratio in a longitudinal direction. One advantage of this construction is that as the longitudinal fibers degrade, they are replaced with permanent and prominent scar tissue. Unlike the original sling fibers, the scar tissue naturally expands and contracts to accommodate physiological changes, such as body growth and patient movement. According to another advantage of the invention, at least some of the sling fibers are non-biodegradable and remain to enhance the support provided by the scar tissue. In this way, the sling fibers initially provide the needed anatomical support, encourage scar tissue formation, and ultimately substantially give way to enable the body's natural tissues to provide most of the needed anatomical support.

In one configuration, the ratio of biodegradable/non-biodegradable fibers in a longitudinal direction (e.g., a direction extending across the urethra as opposed to along the urethra) is greater than about ¼, ⅓, ½, ¾, or 1. In some configurations, the ratio of biodegradable/non-biodegradable fibers in a longitudinal direction is greater than about 2, 3 or 4. According to further configurations, the overall ratio of biodegradable/non-biodegradable fibers is greater than about ¼, ⅓, ½, ¾, 1, 2, 3 or 4.

According to another embodiment, some of the sling fibers are composite fibers including a non-biodegradable core and an outer biodegradable layer. The composite fibers may be formed, for example, by co-extrusion or by dipping, coating or otherwise treating the non-biodegradable core to provide the outer biodegradable layer. The composite fibers may be interleaved with non-biodegradable and/or biodegradable fibers to form a sling for supporting a patient's urethra or for supporting the patient's pelvic floor. One advantage of the composite fibers is that as the outer layer degrades, the size of the pores/interstitial gaps between the fibers effectively increases, providing more room for tissue in-growth and scar tissue formation. The composite fibers may be employed as longitudinal and/or transverse fibers in the sling of the invention.

According to various configurations, the pores/interstitial gaps between adjacent longitudinally extending fibers and/or between adjacent transversely extending fibers are greater than about 50 micrometers (μm), 75 μm, 100 μm, 200 μm or 500 μm subsequent to degradation of the composite fiber outer layer. According to a further configuration, the fibers used to form the mesh sling have an initial diameter of between about 0.005 cm and about 0.1 cm. In some instances, the fibers have an initial diameter of between about 0.01 cm and about 0.05 cm. According to various constructions, the sling may have an initial width of between about 1 cm to about 4 cm, about 4 cm to about 6 cm, about 6 cm to about 8 cm, or larger, depending on the anatomical location to be supported. The slings of the invention may have an initial length of about 4 cm to about 6 cm, about 6 cm to about 8 cm, about 8 cm to about 12 cm, about 12 cm to about 16 cm, or larger, depending on the anatomical location to be supported.

The non-biodegradable portions of the sling may be fabricated from any of a plurality of biocompatible materials, such as nylon, silicone, polyethylene, polyester, polyethylene, polyurethane, polypropylene, polyvinyl polymers, fluoropolymers, copolymers thereof, combinations thereof, or other suitable synthetic material(s). The biodegradable portions of the sling may be derived from mammalian tissue, synthetic materials, or a combination of mammalian tissue and synthetic material. According to some configurations, the biodegradable portions of the sling are formed from synthetic polymers, such as polylatic acid, polyglycolic acid, or natural polymers, such as collagen, cellulose, polypeptides, polysaccharides, or copolymers thereof. According to some configurations, bioactive compounds or drugs may be added to the biodegradable polymers to enhance acute inflammation and encourage scar tissue formation. Examples of these inflammation promoters are fibrinogen and fibrin.

The sling may incorporate or be coated with one or more agents to provide a therapeutic effect, for example, to reduce discomfort, to reduce the chance of infection and/or to promote tissue growth. According to some embodiments, the one or more agents may be disposed between the sling fibers and/or between the two sling layers.

These and other features, advantages and aspects of the invention are described below with respect to the various illustrative embodiments of the invention.

BRIEF DESCRIPTION OF THE DRAWINGS

Various illustrative embodiments of the invention are described below with reference to the appended drawings, which may not be drawn to scale and in which like parts are designated by like reference designations.

FIGS. 3A and 3B are conceptual drawings illustrating an exemplary sling having biodegradable and non-degradable fibers prior and subsequent to degradation of the biodegradable fibers.

DESCRIPTION OF ILLUSTRATIVE EMBODIMENTS

As described in summary above, in various illustrative embodiments, the invention is directed to a supportive sling formed from a material that encourages prominent and permanent formation of scar tissue upon sling implantation and optimizes the sling tension post-surgery using a combination of non-biodegradable and biodegradable materials.

Figure 1:
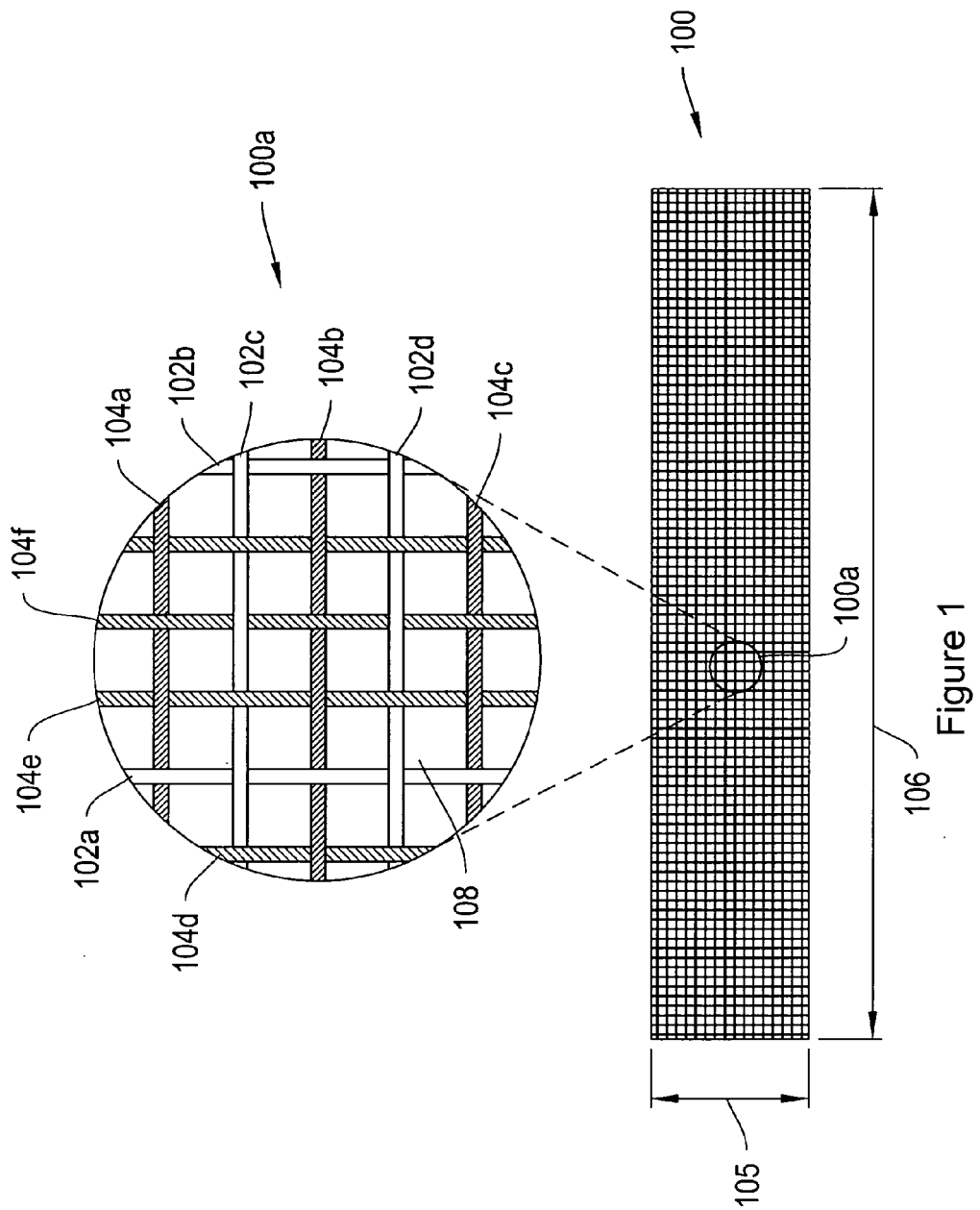
FIG. 1 shows an implantable supportive sling including both non-biodegradable and biodegradable fibers.

FIG. 1 shows exploded section 100a of an implantable supportive sling 100 having both non-biodegradable 102a-102d and biodegradable 104a-104f fibers according to an illustrative embodiment of the invention. As shown, in the embodiment of FIG. 1, the biodegradable 104a-104f and non-biodegradable 102a-102d fibers are interdispersed with each other. The fibers 102a-102d and 104a-104f may be, for example, braided, knitted or otherwise woven together. The sling fibers 102a-102d and 104a-104f may be formed from one or more filaments, which may be made from one or more materials, or may be formed as mono filaments. According to the illustrative embodiment, the sling 100 has an initial tension and expansion capability when implanted into the body of a patient. Subsequent to implantation, the fibers 104a-104f degrade and are absorbed into the tissue surrounding the sling 100. As fibers 104a-104f are removed from the sling 100, the sling 100 is able to stretch/expand more easily.

According to one aspect, the material used for the fibers 104a-104f is selected so as to have a pre-determined rate of degradation, so that their degradation is timed to coincide with the growth of permanent and prominent scar tissue on, into and around the sling 100. The scar tissue forms a natural support that takes the place of the degraded fibers 104a-104f. The scar tissue acts both to maintain the initial support provided by the sling 100 and to enable the sling 100 to stretch/expand and contract naturally as may be needed to accommodate physiological changes in the body of the patient, thereby providing for enhanced sling tension attenuation. Such physiologic changes include, for example, weight loss, weight gain, body growth (particularly important when treating adolescents), and patient movement. According to another advantage of the invention, the non-biodegradable sling fibers 102a-102d remain to enhance the anatomical support provided by the scar tissue.

According to the illustrative embodiment, the sling 100 has a high biodegradable/non-biodegradable fiber ratio in a longitudinal direction 106 (e.g., a direction extending across the urethra as opposed to along the length of the urethra). This feature is particularly advantageous when providing urethral support or for supporting the pelvic floor. For example, as the longitudinal fibers (e.g., the fibers 104a-104f) degrade, they are replaced with scar tissue, which naturally expands and contracts to maintain the appropriate support under the urethra or pelvic floor, even in light of physiological changes. In one configuration, the ratio of biodegradable/non-biodegradable fibers in the longitudinal direction 106 is greater than about ¼, ⅓, ½, ¾, or 1, or greater than about 1. In some configurations, the ratio of biodegradable/non-biodegradable fibers in the longitudinal direction 106 is greater than about 2, 3 or 4. According to further configurations, the over-all ratio of biodegradable/non-biodegradable fibers is greater than about ¼, ⅓, ½, ¾, 1, 2, 3, or 4, or greater than about 4.

According to the illustrative embodiment, the sling 100 includes a plurality of pores/interstitial gaps 108 formed between the fibers 102a-102d and 104a-104f. According to 15 various configurations, the diameter of a given pore/interstitial gap 108 that forms between adjacent longitudinally extending non-degradable fibers (e.g., fibers 102c and 102d) and/or between adjacent transversely extending non-degradable fibers (e.g., fibers 102a and 102b) is greater than about 50 micrometers (μm), 75 μm, 100 μm, 200 μm, 500 μm, 1 mm, or greater subsequent to degradation of the interspersed degradable fibers (e.g., 104b).

According to a further configuration, the fibers used to form the mesh sling have an initial diameter of between about 0.005 cm and about 0.1 cm. In some instances, the fibers have an initial diameter of between about 0.01 cm and about 0.05 cm. According to various constructions, the sling may have an initial width of between about 1 cm to about 4 cm, about 4 cm to about 6 cm, about 6 cm to about 8 cm, or larger, depending on the anatomical location to be supported. The slings of the invention may have an initial length of about 4 cm to about 6 cm, about 6 cm to about 8 cm, about 8 cm to about 12 cm, about 12 cm to about 16 cm, or larger, depending on the anatomical location to be supported.

According to one feature, the degradation products of the biodegradable materials accelerate tissue inflammation and, thus, scar tissue formation in the region of the implanted sling.

Figure 2:
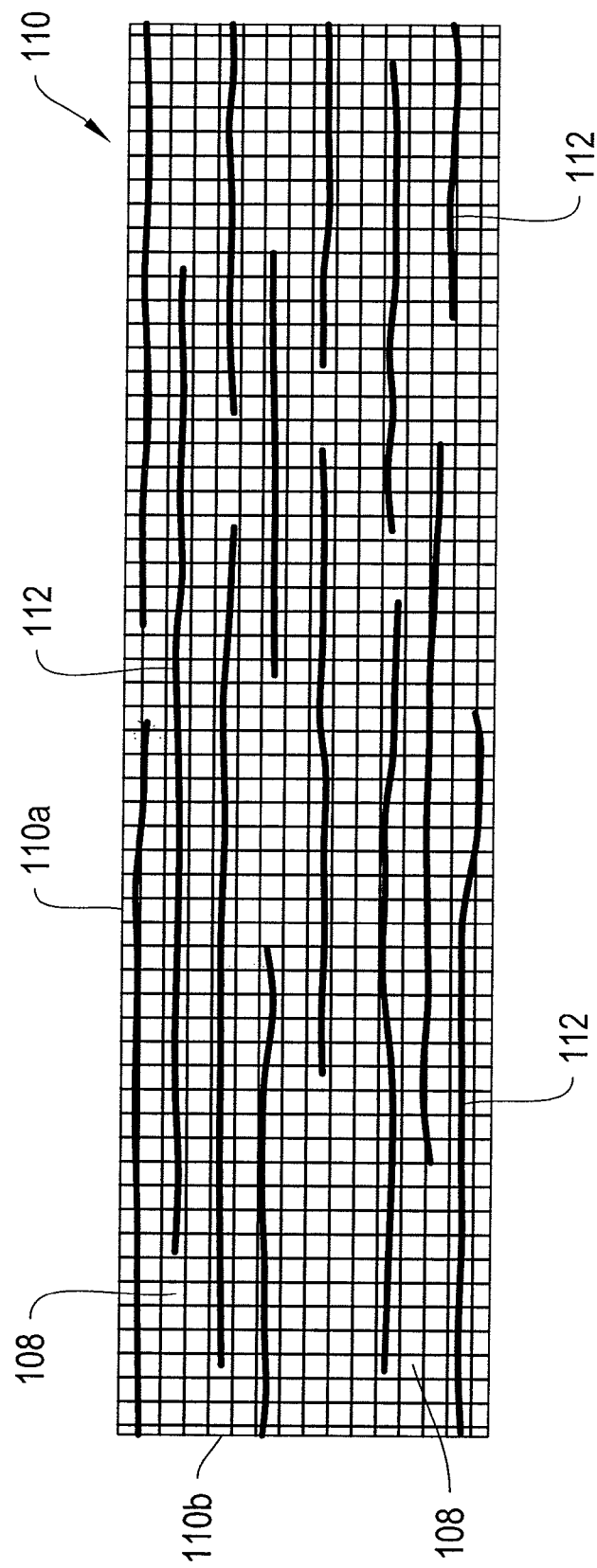
FIG. 2 shows an implantable supportive sling including both non-biodegradable and biodegradable fibers.

As shown in FIG. 1, the fibers 102*a*-d and 104*a*-f are formed in a grid-like pattern, with one or more transverse 102*a* and one or more longitudinal 102*c* fibers extending in the transverse direction 105 (e.g., in a direction along the length of the urethra) and longitudinal direction 106. The degradable and non-degradable fibers may extend in either or both directions 105 and 106. In certain embodiments, the fibers are configured as a mesh having a non-degradable grid-like formation with degradable fibers interwoven through gaps and holes within the mesh. FIG. 2 depicts an example of such an alternative embodiment. The mesh 110, which is configured in a grid-like fashion similar to FIG. 1, includes longitudinal 110*a* and transverse 110*b* strands of non-degradable fibers configured in a grid-like fashion. Holes 108 form the interstitial spaces between the strands, similar to the holes 108 shown in FIG. 1. As shown in the embodiment of FIG. 2, biodegradable fibers 112 are woven through the holes 108, extending under and over the strands 110*a* and 110*b* and being supported by the strands 110*a* and 110*b* and to rest within the mesh. As described above, as the degradable strands 112 degrade, the remaining mesh strands become less restricted and the mesh 110 becomes more elastic, thereby allowing the mesh 110 to stretch and expand more easily. As the fibers 112 degrade, scar tissue forms within the spaces vacated by the strands 112 and forms natural support described above.

FIGS. 3A and 3B depict an alternative configuration of a sling 120 having biodegradable and non-degradable components, similar to the slings described above. As shown in FIG. 3A, the mesh 120 has non-degradable strands 122 extending in the transverse direction 105 (e.g., in a direction along the length of the urethra), and a number of non-degradable segments 123 extending between transverse strands, such as strand 123, in the longitudinal direction 106. The mesh 120 also includes longitudinally extending biodegradable fiber segments 124*a*-124*h* that cross or otherwise pass between transverse fibers in the longitudinal direction 106. In the depicted embodiment, the degradable segments 124*a*-124*h* are positioned adjacent to one or more longitudinally extending non-degradable fibers (e.g., fiber 124*a* is positioned adjacent to strands 125 and 127). Alternatively, one or more degradable segments can be positioned adjacent to longitudinally extending degradable fibers. As shown, various longitudinal degradable segments, such as 124*a* and 124*b*, extend in substantially the same longitudinal path (e.g., both strands 124*a* and 124*b* extend substantially parallel to an exterior edge 120*a* of the sling 120) but are spaced apart so as to not contact a common transverse strand. As shown in FIG. 3B, after degradation of the longitudinally extending biodegradable strands 124*a*-124*h*, large holes 128 are left between the non-degradable fibers, for example between strands 125 and 127.

The mesh 120 is formed, in one implementation, by attaching the cross-segments (e.g., 124*a* and 124*b*) to the transverse strands by adhesive, laser welding, or a patterned air-drying technique. According to one embodiment, the air-drying technique begins with dissolving a biodegradable polymer in a solvent, then applying the solvent to a non-biodegradable mesh. Following application of the solvent to the mesh, the solvent is allowed to evaporate, leaving the biodegradable polymer in place and secured to the mesh. The mesh and applied polymer may be air-dried to allow for evaporation of the solvent. In certain embodiments, any suitable method may be used to accelerate evaporation of the solvent from the polymer and mesh, such as machine-drying and applying heat. According to one feature, the air-drying technique allows for precise placement of the biodegradable polymers to selected locations on the mesh.

The biodegradable polymer may be applied to the mesh sling in a selected pattern. For example, the mesh sling may be constructed such that it has a plurality of apertures spaced along the length of the sling, and the biodegradable polymer may be applied to the mesh such that it bridges the apertures. The biodegradable polymer may be applied to the sling in a plurality of segments, such as segments 124*a*-124*h* of FIG. 3A, and the segments may be positioned to form a plurality of v-shapes, triangles, diamond shapes, polygonal shapes, ellipses, circles, or a combination of shapes, extending along at least a portion of the length of the sling. The shapes may extend from the center of the sling to an end of the sling. The biodegradable polymer may also be applied as longitudinal strands extending along a length of the sling, crossing over transverse mesh strands. In other embodiments, the biodegradable polymer may be applied as transverse strands. According to various implementations, the biodegradable polymer may be applied to any selected section of the mesh sling. For example, the biodegradable polymer may be applied to the ends of the sling and not to the center portion of the sling, or the biodegradable polymer may be applied along the entire length of the sling.

Figure 4:
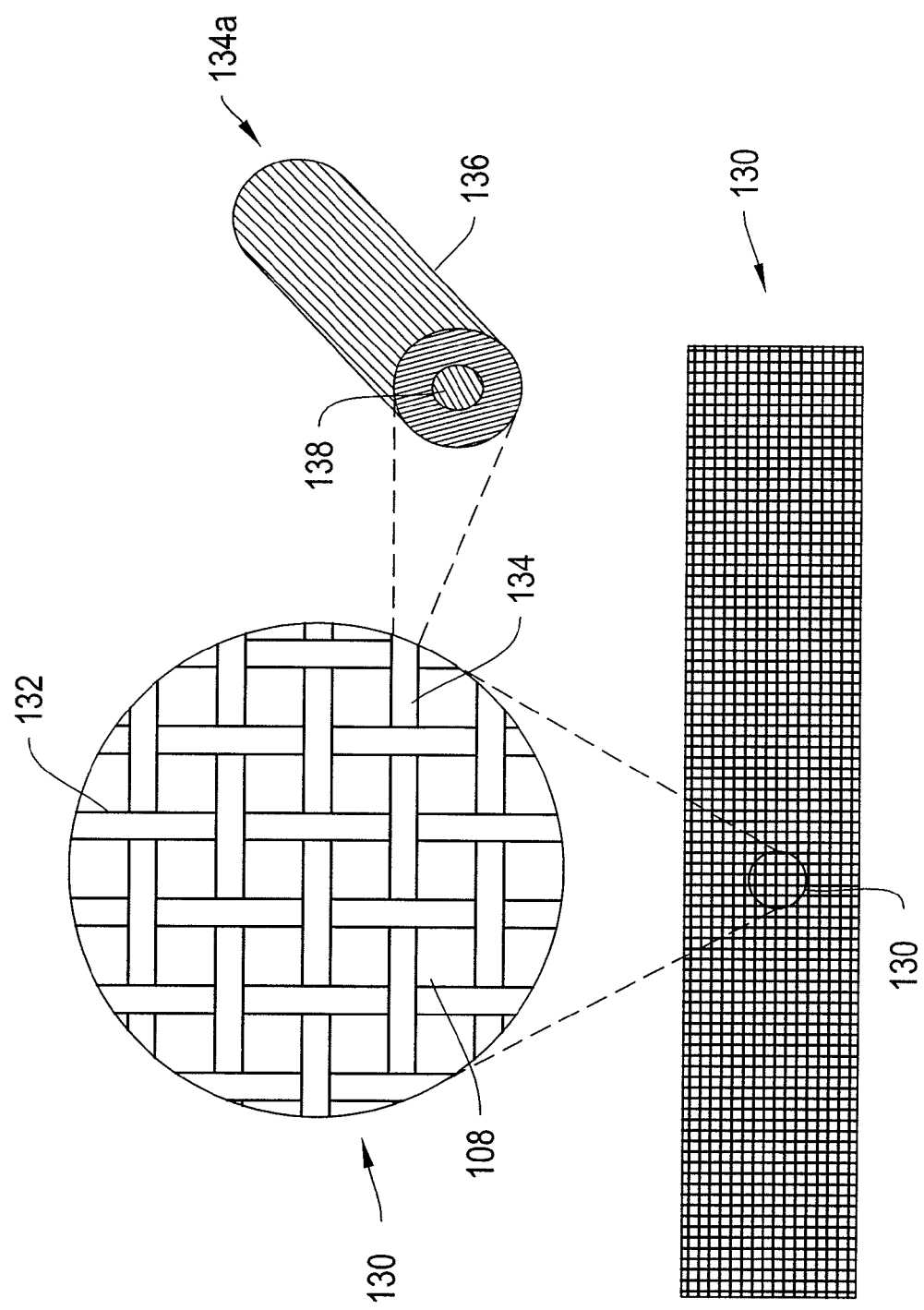
FIG. 4 shows an implantable supportive sling including composite fibers having a non-biodegradable core and a biodegradable outer layer.

In certain exemplary implementations, the mesh according to the invention is formed from fibers that are coextruded or otherwise configured as single strands having both non-degradable and degradable components. FIG. 4 depicts an exemplary embodiment of such a mesh 130. As shown in the exploded cross-sectional view of subsection 134*a* of the longitudinal strand 134, the fibers 132 and 134 of mesh 130 have an interior non-degradable component 138 disposed within a degradable exterior portion 136. Pores/interstitial gaps 108 form between adjacent longitudinally extending fibers 134 and/or between adjacent transversely extending fibers 132. The pores 108 have a diameter greater than about 50 micrometers (μm), 75 μm, 100 μm, 200 μm or 500 μm subsequent to degradation of the fiber outer layer 136. In certain embodiments, the pores expand by about 5% or greater, 10% or greater, 25% or greater, or 50% or greater upon degradation of the outer layer.

The strand 134 is depicted in subsection 134*a* as extending longitudinally, though it can also be incorporated in one or more of the transverse strands 132, allowing the entire mesh 130 to be formed from strands of this composite material.

In certain configurations, the composite of mesh 130 is incorporated with other mesh embodiments described herein. For example, the composite material of mesh 130 may be used to form the degradable segments 124*a* through 124*h* shown in FIG. 3A. In such an implementation, as the exterior segment 136 degrades, the thin non-absorbable filaments of strand 138, rather than the gaps 128 shown in FIG. 3B, are left behind. The remaining mesh is accordingly more pliable and flexible than prior to the degradation. In another example, one or more of the composite strands used in mesh 130 are used as the biodegradable strand in mesh 100 or 120. In another example, the mesh 130 may incorporate one or more of strands 102*a*-d and 104*a*-f of the sling mesh 100, such that the one or more of strands 102*a*-d and 104*a*-f are interspersed with strands 132 and 134. In another example, the mesh 130 is configured to include one or more of segments 124 and 125 of mesh 120, which impart further initial strength to the mesh 130 but allow for subsequent pliability after the degradation.

Exemplary mesh materials include, for example, synthetic materials, natural materials (e.g., biological) or a combination thereof. The non-degradable portion of the mesh may be fabricated from any of a number of non-degradable biocompatible materials, such as nylon, silicone, polyethylene, polyester, polyethylene, polyurethane, polypropylene, fluoropolymers, copolymers thereof, combinations thereof, or other suitable synthetic material(s). The biodegradable component of the mesh may be any suitable biodegradable material. The biodegradable material may be, for example, a biodegradable synthetic material. The term "biodegradable," is used synonymously with "bioabsorbable" and with "degradable" herein, and refers to the property of a material that dissolves in the body or is absorbed into the body.

Suitable bioabsorbable synthetic materials include, without limitation, polylactic acid (PLA), polyglycolic acid (PGA), poly-L-lactic acid (PLLA), poly(amino acids), polypeptides, human dermis and decellularized animal tissue. Human tissues may be derived, for example, from human cadaveric or engineered human tissue. Animal tissues may be derived, for example, from porcine, ovine, bovine, and equine tissue sources. The material may be an omnidirectional material, a material that has equivalent tensile strength from any direction, such as pericardium or dermis. Alternatively, the material may be an oriented material, a material that has a single direction where the tensile strength of the material is the highest. Oriented materials may include rectus fascia and/or facia lata.

Exemplary biodegradable polymers, which may be used to form a mesh, in addition to those listed above, include, without limitation, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLAIPLA), poly(L-lactide-coglycolide) (PLLA/PGA), poly(D,L-lactide-coglycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tertbutyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[ (97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as poly(lysine), Poly(glutamic acid), gelatin and collagen; and mixtures and copolymers thereof In various implementations of the invention, the mesh, either as a whole or on a fiber by fiber basis (e.g., fibers 122, 125, etc.), may include an agent for release into the patient's tissues. One illustrative agent is a tissue growth factor that promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the biodegradable materials. This may be controlled by selecting differing methods for loading the agent onto the sling. The tissue growth factor may include natural and/or recombinant proteins for stimulating a tissue response so that collagenous tissue such as scar tissue growth is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salecetamide, salicylamine o-acetic acid, salicylsulfuric acid, salsalate and sulfasalazine; thiazinecarboxamides such as droxicam, isoxicam, piroxicam and tenoxicam; others such as E-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof. Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the slings of the invention include, but are not limited to, aceclofenac, acetaminophen, acetaminosalol, acetanilide, acetylsalicylsalicylic acid, alclofenac, alrninoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, pbromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

According to another feature, the mesh of the invention may include any suitable end portions, such as tissue dilators, anchors, and association mechanisms for associating the sling with a delivery device. Without limitation, examples of slings, sling assemblies, sling delivery devices and approaches, sling assembly-to-delivery device association mechanisms, and sling anchoring mechanisms including features with which the sling of the invention may be employed are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No.

10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 101774,842, entitled "Devices for minimally invasive pelvic surgery," U.S. patent application Ser. No. 101774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof" Moreover, the slings disclosed herein may be adapted for use in pelvic floor repair systems and related devices and methods. Such systems include, for example, those disclosed in U.S. Pat. No. 6,197,036, entitled "Pelvic Floor Reconstruction," U.S. Pat. No. 6,691,711, entitled "Method of Correction of Urinary and Gynecological Pathologies Including Treatment of Incontinence," U.S. Pat. No. 6,884,212, entitled "Implantable Article and Method," U.S. Pat. No. 6,911,003, entitled "Transobturator Surgical Articles and Methods," U.S. patent application Ser. No. 10/840,646, entitled "Method and Apparatus for Cystocele Repair," U.S. application 10/834,943, entitled "Method and Apparatus for Treating Pelvic Organ Prolapse," U.S. Patent Application Serial No. 10/804,718, entitled "Prolapse Repair," and U.S. patent application Ser. No. 11/115,655, entitled "Surgical Implants and Related Methods," U.S. patent application Ser. No. 11/400,111, entitled "Systems, Devices, and Methods for Treating Pelvic Floor Disorders," and U.S. patent application Ser. No. 11/399,913, entitled "Systems, Devices, and Methods for Sub-Urethral Support," the entire contents of all of which are incorporated herein by reference.

The foregoing embodiments are merely examples of various configurations of the materials described and disclosed herein. Additional configurations can be readily deduced from the foregoing, including combinations thereof, and such configurations and continuations are included within the scope of the invention. The specifications and other disclosures in the patents, patent applications, and other references cited herein are hereby incorporated by reference in their entirety.

What is claimed is:

1. A mesh for use in an implantable sling, the mesh comprising:
    a plurality of transverse strands;
    a plurality of longitudinal strands, the plurality of transverse strands and the plurality of longitudinal strands being arranged in a grid; and
    a plurality of biodegradable fiber segments extending in a substantially same longitudinal path that is parallel with the longitudinal strands, the plurality of biodegradable fiber segments being spaced apart in the grid such that no two segments of the plurality of biodegradable fiber segments contact a common transverse strand.

2. The mesh of claim 1, wherein the plurality of transverse strands are non-degradable.

3. The mesh of claim 1, wherein at least one segment of the plurality of biodegradable fiber segments has an inner non-degradable core disposed within an exterior degradable shell.

4. The mesh of claim 1, comprising a plurality of biodegradable longitudinal strands.

5. The mesh of claim 1, wherein the plurality of longitudinal strands include both biodegradable strands and non-degradable strands, and the plurality of transverse strands include both biodegradable strands and non-degradable strands.

6. The mesh of claim 1, wherein at least one biodegradable strand has an inner non-degradable core disposed within an exterior degradable shell.

7. The mesh of claim 5, wherein, upon degradation of at least one biodegradable strand, a gap of greater than about 50 µm forms in the mesh between mesh strands adjacent the at least one biodegradable strand.

8. The mesh of claim 1, wherein the plurality of biodegradable fiber segments include a material that degrades in-vivo at a rate that facilitates a predetermined rate of scar tissue in-growth into the mesh.

9. The mesh of claim 1, wherein the plurality of longitudinal strands includes both biodegradable strands and non-degradable strands, and wherein a ratio of biodegradable strands to non-degradable strands is greater than about ¼.

10. The mesh of claim 1, wherein the plurality of longitudinal strands includes both biodegradable strands and non-degradable strands, and wherein a ratio of biodegradable strands to non-degradable strands is in a range of about ¼ to about 1.

11. The mesh of claim 1, comprising a plurality of biodegradable strands and a plurality of non-degradable strands, and wherein a ratio of biodegradable strands to non-degradable strands is greater than about ¼.

12. The mesh of claim 1, comprising a plurality of biodegradable strands and a plurality of non-degradable strands, and wherein a ratio of biodegradable to non-degradable strands is in a range of about ¼ to about 4.

13. The mesh of claim 1 including an agent.

14. The mesh of claim 13, wherein the agent is a therapeutic agent.

15. The mesh of claim 1, wherein at least one transverse strand is attached to two or more of the plurality of longitudinal strands by an adhesive.

16. The mesh of claim 1, wherein at least a portion of the plurality of longitudinal strands is adapted to extend along a patient's urethra.

17. A mesh for use in an implantable sling, the mesh comprising:
- a plurality of non-degradable transverse strands;
- a first plurality of fiber segments, the first plurality of fiber segments being non-degradable and extending in a first longitudinal path that is perpendicular to the transverse strands, the first plurality of fiber segments being spaced apart in the mesh such that no two segments of the first plurality of fiber segments contact a common transverse strand; and
- a second plurality of fiber segments, the second plurality of fiber segments being biodegradable and extending in a second longitudinal path that is perpendicular to the transverse strands and parallel with the first longitudinal path, the second plurality of fiber segments being spaced apart in the mesh such that no two segments of the second plurality of fiber segments contact a common transverse strand.

18. The mesh of claim 17, wherein the first longitudinal path is different than the second longitudinal path.

19. The mesh of claim 17, wherein the second plurality of fiber segments include a therapeutic agent.

20. The mesh of claim 17, wherein the second plurality of fiber segments include a material that degrades in-vivo at a rate that facilitates a predetermined rate of scar tissue in-growth into the mesh.

* * * * *